(12) United States Patent
Wass et al.

(10) Patent No.: US 7,222,548 B2
(45) Date of Patent: May 29, 2007

(54) ELEVATED BLACK PANEL FOR ACCELERATED WEATHERING TEST DEVICE

(75) Inventors: Chris Wass, North Riverside, IL (US); Richard Schultz, Chicago, IL (US); Mikhail Rokhlenko, Skokie, IL (US)

(73) Assignee: Atlas Material Testing Technology, L.L.C., Chicago, IL (US)

( * ) Notice: Subject to any disclaimer, the term of this patent is extended or adjusted under 35 U.S.C. 154(b) by 281 days.

(21) Appl. No.: 11/082,594

(22) Filed: Mar. 17, 2005

(65) Prior Publication Data
US 2006/0207352 A1  Sep. 21, 2006

(51) Int. Cl.
*G01N 17/00* (2006.01)
(52) U.S. Cl. .................. 73/865.6; 73/159; 374/208
(58) Field of Classification Search ................. 374/208
See application file for complete search history.

(56) References Cited

U.S. PATENT DOCUMENTS

| | | | |
|---|---|---|---|
| 4,760,748 A | 8/1988 | Katayanagi et al. | |
| 4,807,247 A | 2/1989 | Robbins, III | |
| 4,957,011 A | 9/1990 | Huber et al. | |
| 5,138,892 A | 8/1992 | Suga | |
| 5,399,018 A * | 3/1995 | Hollander et al. | .......... 374/121 |
| 5,476,636 A | 12/1995 | Tomiita et al. | |
| 5,503,032 A | 4/1996 | tikhtman et al. | |
| 2004/0007049 A1 | 1/2004 | Hoppach | |
| 2004/0093965 A1 | 5/2004 | Hardcastle, III | |
| 2004/0123682 A1 | 7/2004 | Grossman et al. | |

FOREIGN PATENT DOCUMENTS

JP  408055511 A  2/1996

* cited by examiner

*Primary Examiner*—Robert Raevis
(74) *Attorney, Agent, or Firm*—Vedder Price Kaufman & Kammholz

(57) ABSTRACT

A black panel assembly for use in an accelerated weathering test device having a specimen table includes a platform disposed on the specimen table, the platform including a plurality of standoffs and a mounting surface, wherein the plurality of standoffs elevate the mounting surface relative to the specimen table. The black panel assembly additionally includes a black panel having an exposure side and a mounting side, wherein the black panel is mounted on the platform from the mounting side. The black panel assembly further includes a temperature sensor connected to the exposure side of the black panel.

14 Claims, 5 Drawing Sheets

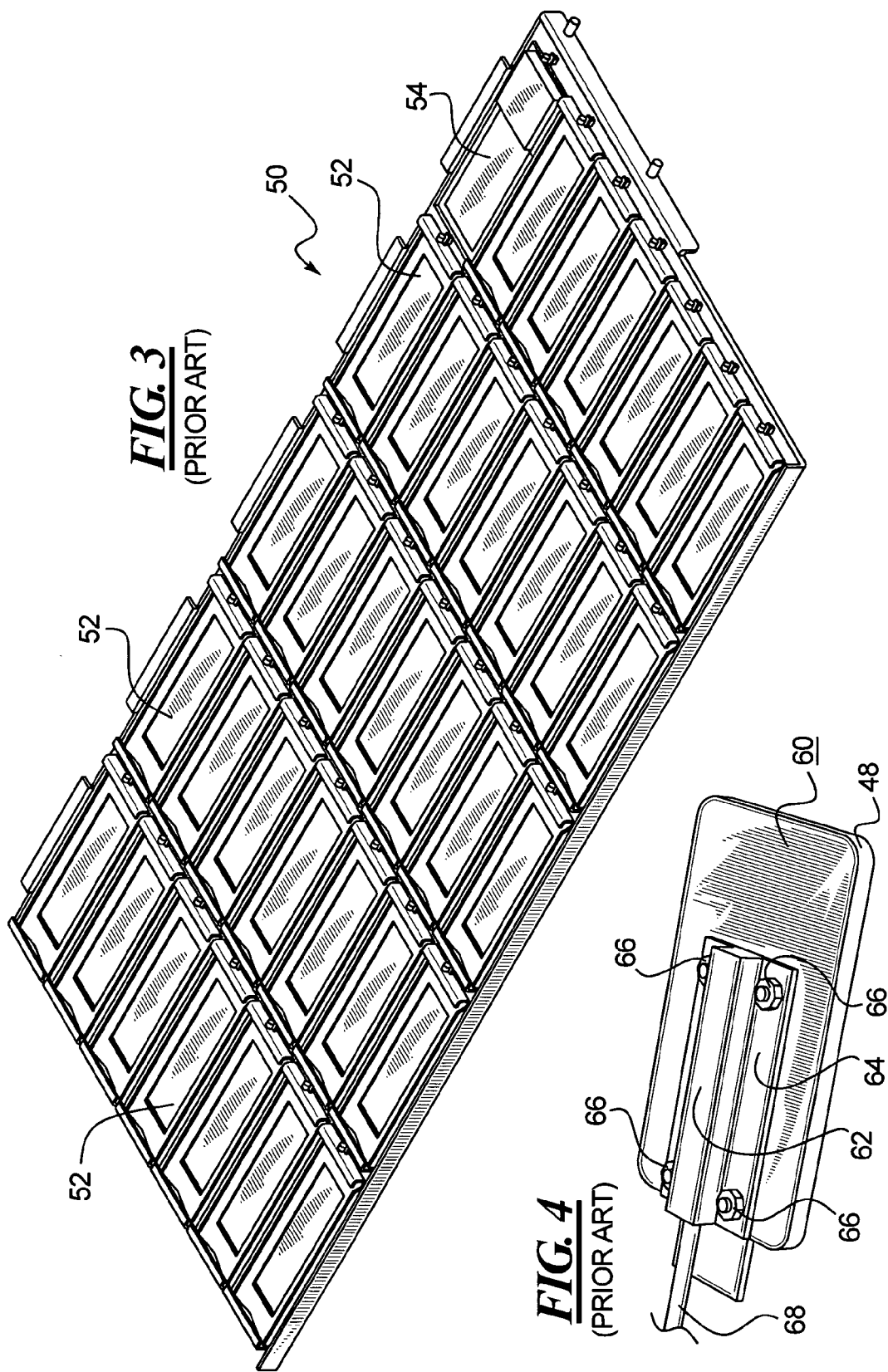

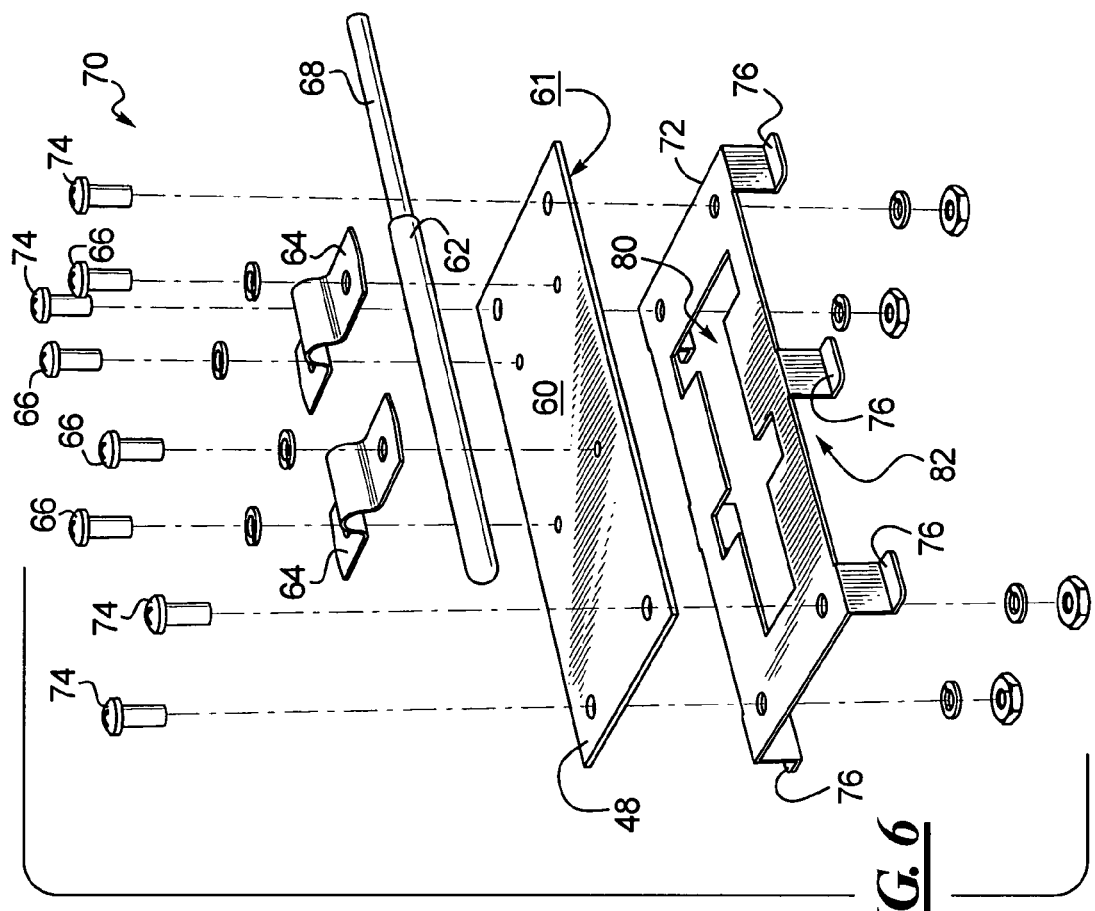
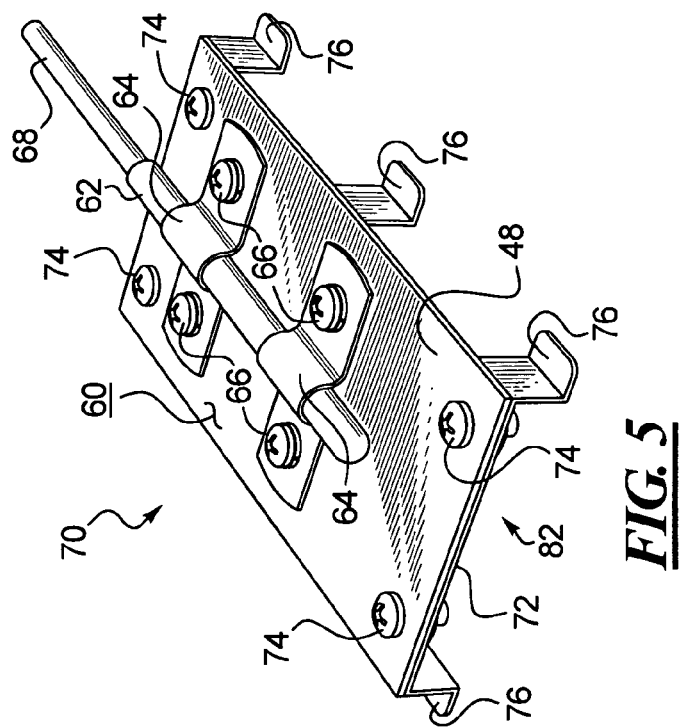

ELEVATED BLACK PANEL FOR ACCELERATED WEATHERING TEST DEVICE

FIELD OF THE DISCLOSURE

The present disclosure relates to accelerated weathering test devices, and more particularly related to an elevated black panel for accelerated weathering test devices.

BACKGROUND

Manufacturers of exterior coatings, such as paints and finishes, as well as plastics and other components which tend to degrade under exposure to solar radiation and other weathering effects, often want to know how such products will perform following years of exposure. However, such manufacturers typically require such information in a much shorter time than it would take to expose such materials to weathering effects under normal conditions. Accordingly, accelerated weathering test devices have been developed which accelerate the effects of weathering due to outdoor exposure in a much shorter time so that manufacturers need not actually wait five or ten years in order to determine how their products will hold up after five or ten years of actual outdoor exposure.

Weathering test devices can be categorized into outdoor devices that utilize solar radiation for testing, and indoor devices that generate artificial radiation for testing. Indoor test devices typically include a test chamber, in which test specimens can be exposed to accelerated weathering conditions. These test chambers typically include one or more sources of artificial radiation, such as high intensity plasma lamps, that can direct high intensity radiation toward test specimens that are placed in the test chambers. Additionally, indoor accelerated weathering test devices include a black panel temperature probe that is disposed in the test chamber near the test specimens. The black panel temperature probe typically includes a black painted metallic panel that has a temperature probe mounted thereon. The temperature sensed from the black panel temperature probe typically represents the highest temperature that may be experienced by the test specimens during accelerated weathering tests.

A type of indoor accelerated weathering test device that is commonly used includes a test chamber, in which the test specimens are horizontally arranged on static arrays of specimen trays. These weathering test devices include a generally rectangular test chamber having a ceiling, a floor and a pair of side walls. One or more high intensity plasma lamps, such as Xenon lamps are typically positioned in the ceiling and configured to direct radiation toward the floor of the test chamber. The specimen trays are placed near the floor of the test chamber so that an exposed surface of each specimen receives radiation from the lamps. However, the bottom sides of the test specimens are not exposed to any airflow that may be present in the test chamber. The black panel temperature probe is placed in one of the test specimen trays, and similarly, the bottom side thereof is not exposed to or airflow in the test chamber.

The ASTM 6151 (American Society for Testing and Materials, designation 6151), which is directed to standard practice for exposing nonmetallic materials in accelerated test devices that use laboratory light sources, advises that the back side of the black panel "shall be open to the atmosphere within the exposure chamber." However, in the above-described indoor accelerated weathering test device, the back side of the black panel is not open to the atmosphere within the exposure chamber. Accordingly, the black panel may experience static and dynamic temperatures that are unrealistic compared to the actual temperatures that are experienced by the test specimens.

Therefore, there exists a need in the art for a black panel that can be placed in the above-described type of indoor accelerated weathering test device such that the backside of the black panel is open to the atmosphere within the exposure chamber of the device.

SUMMARY

In accordance with one principal aspect of the present disclosure, a black panel assembly for use in an accelerated weathering test device having a specimen table includes a platform disposed on the specimen table, the platform including a plurality of standoffs and a mounting surface, wherein the plurality of standoffs elevate the mounting surface relative to the specimen table. The black panel assembly additionally includes a black panel having an exposure side and a mounting side, wherein the black panel is mounted on the platform from the mounting side. The black panel assembly further includes a temperature sensor connected to the exposure side of the black panel.

In accordance with another principal aspect of the present disclosure, an accelerated weathering test device having a test chamber including a specimen table, and at least one lamp assembly disposed in the test chamber and configured to direct irradiance toward the specimen table includes a platform disposed on the specimen table, the platform including a plurality of standoffs and a mounting surface, wherein the plurality of standoffs elevate the mounting surface relative to the specimen table. The accelerated weathering test device additionally includes a black panel having an exposure side and a mounting side, wherein the black panel is mounted on the platform from the mounting side, and a temperature sensor connected to the exposure side of the black panel.

In accordance with another principal aspect of the present disclosure, a black panel assembly for use in a test chamber of an accelerated weathering test device having at least one lamp directing irradiance toward a specimen table includes a platform disposed on the specimen table, the platform including a plurality of standoffs and a flat mounting surface, wherein the plurality of standoffs elevate the mounting surface relative to the specimen table to provide a gap between a bottom of the mounting surface and the specimen table, and wherein the standoffs are configured to allow air to flow through the gap. The black panel assembly further includes a black panel having an exposure side and a mounting side, the black panel configured to be mounted on the platform from the mounting side, the exposure side of the black panel oriented to receive irradiance from the at least one lamp. The black panel assembly additionally includes a temperature sensor connected to the exposure side of the black panel.

BRIEF DESCRIPTION OF THE DRAWINGS

Certain embodiments are shown in the drawings. However, it is understood that the present disclosure is not limited to the arrangements and instrumentality shown in the attached drawings, wherein:

FIG. 3 illustrates a perspective view of an array of specimen trays for use in the test chamber of FIG. 2;

FIG. 4 illustrates a perspective view of a black panel for use in the test chamber of FIG. 2;

FIG. 5 illustrates a perspective view of a black panel assembly constructed in accordance with the teachings of the present disclosure;

FIG. 6 illustrates an exploded view of the black panel assembly of FIG. 5; and

DETAILED DESCRIPTION

Figure 1:
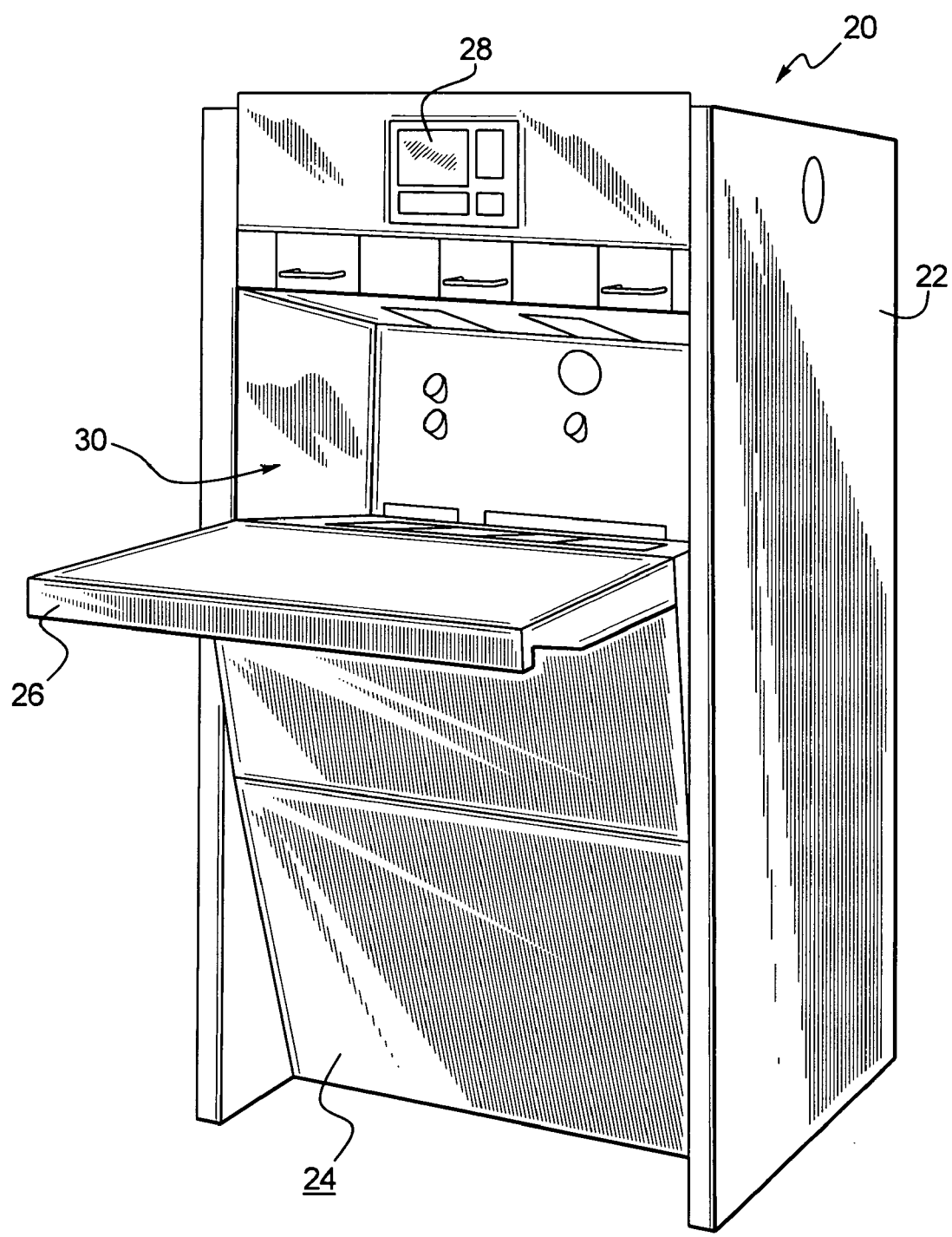
FIG. 1 illustrates a perspective view of an accelerated weathering test device.

For the purposes of promoting and understanding the principles disclosed herein, reference will now be made to the preferred embodiments illustrated in the drawings and specific language will be used to describe the same. It will nevertheless be understood that no limitation of the scope is thereby intended. Such alterations and further modifications in the illustrated device and such further applications are the principles disclosed as illustrated therein as being contemplated as would normally occur to one skilled in the art to which this disclosure relates.

Referring to FIG. 1, a prior art accelerated weathering test device 20 is generally shown. The device 20 includes a cabinet 22, in which the components for operating the device 20 are housed. The device 20 includes a front face 24, from which a test chamber door 26 and a control panel 28 can be accessed. The chamber door 26 provides access to a test chamber 30. The control panel 28 allows an operator of the device 20 to control various functions of the device 20. The control panel 28 may include a plurality of control buttons and at least one display. In the disclosed example, the control panel 28 is a touch screen display.

Figure 2:
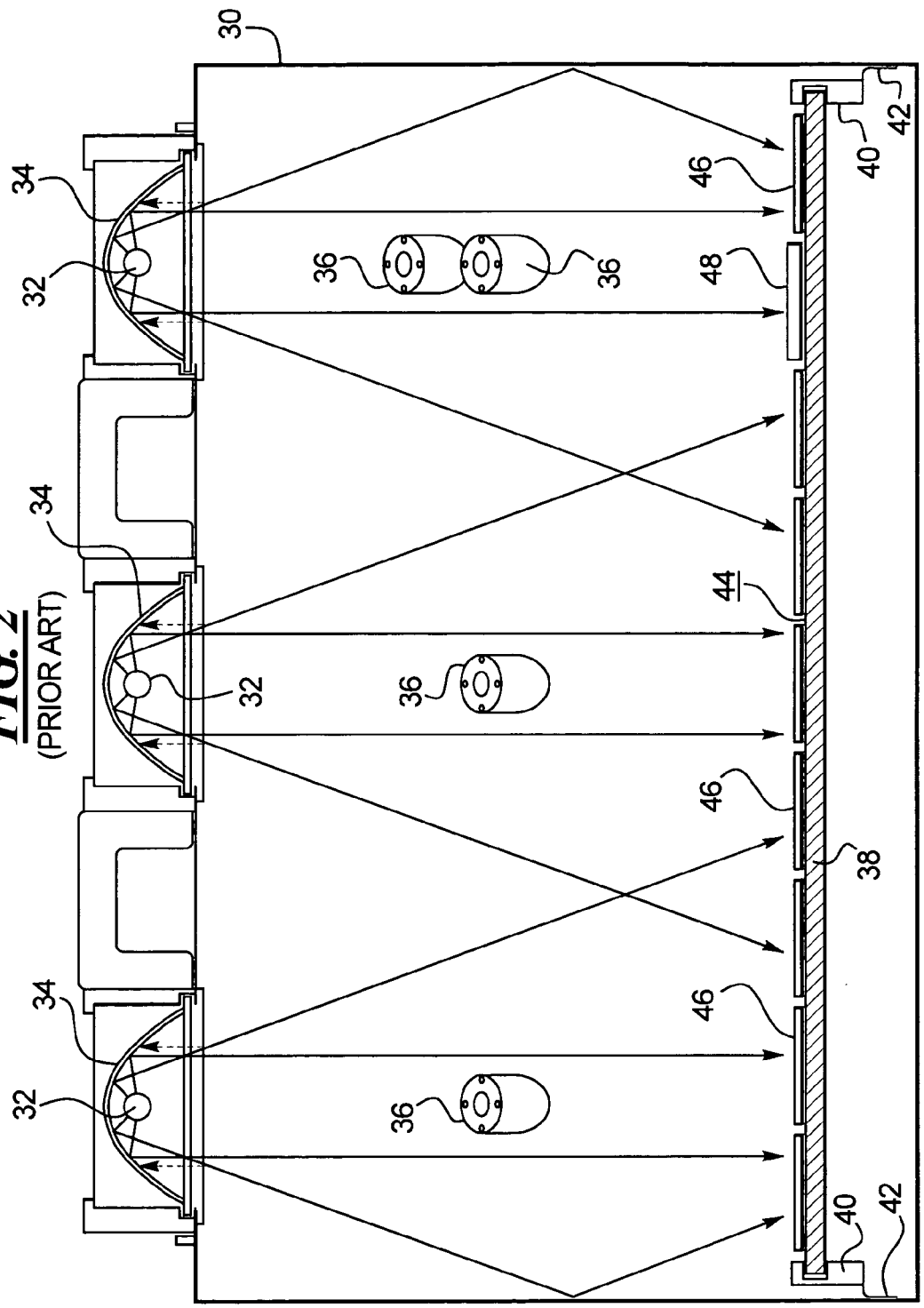
FIG. 2 illustrates a schematic view of the test chamber of the accelerated weathering test device of FIG. 1.

Referring to FIG. 2, a detailed diagram of the test chamber 30 of the device 20 is shown. The test chamber 30 is generally rectangular and includes a plurality of lamps 32 that may be disposed on the ceiling of the test chamber 30. Each lamp 32 includes a reflector 34, which in combination with the lamp 32 direct irradiance toward the bottom of the test chamber 30. On any one of the walls of the test chamber 30, one or more sensors 36 may be disposed that can sense various environmental conditions of the test chamber 30, such as irradiance, humidity, and/or temperature. Near the floor of the test chamber 30, is a specimen table 38 that can slide in and out of the test chamber 30 along the support tracks 40. Accordingly, an operator can open the test chamber door 26 and pull out the specimen table 38 to gain access to the specimen table 38. The support tracks 40 are supported by support brackets 42 that are attached to opposing walls of the test chamber 30.

The specimen table 38 includes a mounting surface 44, on which one or a plurality of test samples 46 can be placed so as to be weather tested in the test chamber 30. A black panel 48 is also placed on the specimen table 38 to provide a reference temperature that reflects the highest temperature the test specimens 46 may experience during testing in the test chamber 30.

Referring to FIG. 3, a prior art array of specimen trays 50 is shown. The array of specimen trays 50 can be sized to occupy a portion or all of the specimen table 38. In the disclosed example, as shown in FIG. 3, the array of specimen trays 50 includes thirty-four individual specimen trays 52 and a single black panel tray 54. Each individual specimen tray 52, is generally rectangular and configured to hold a correspondingly sized test specimen 46. The black panel tray 52 is also sized to hold the black panel 48.

Referring to FIG. 4, a prior art black panel 48 is shown. The black panel 48 includes an exposure side 60 that is covered with a black layer, and a mounting side (not shown) from which the black panel 48 can be mounted or placed on the specimen table 38. The black layer can include any coating that has good resistance to aging and can absorb a majority of the radiation reaching the coating. The black panel 48 includes a temperature sensor housing 62 that is attached to the exposure side 60 with a bracket 64. The temperature sensor housing 62 and the bracket 64 can also be coated with the same black layer as the black panel 48. The bracket 64 is secured to the exposure side 60 with fasteners 66. The temperature sensor housing 62 houses a temperature sensor probe (not shown) that can sense the temperature of the exposure side 60 of the black panel 48. The temperature sensor probe provides signals that are conveyed to the device 20 by temperature sensor wires 68. This thermal sensitive element can be black coated stem type bi-metallic dial sensor or resistance sensor.

Referring back to FIGS. 2 and 3, the black panel 48 can be either mounted in the black panel tray 54, or simply mounted on the specimen table 38. Accordingly, the mounting side of the black panel 48 may be in contact either with the bottom of the black panel tray 54 or the mounting surface 44 of the specimen table 38. Therefore, the mounting side of the black panel 48 is not exposed to any air flow in the test chamber 30.

The exposure side 60 of the black panel 48 is exposed to the radiance provided by the lamps 30. The black panel 48 is typically constructed from a metal that is resistant to corrosion. Accordingly, because the exposure side 60 of the black panel 48 has a black coating and constructed from metal, the temperature of the black panel 48 during weathering tests may be typically higher than the temperature of the test specimens 46. Additionally, because the black panel 48 is mounted on the mounting surface 44 of the specimen table 38, there may be heat conduction between the black panel 48 and the specimen table 38 that may influence the static and dynamic response of the temperature of the black panel 48. Accordingly, such influence on the static and dynamic response of the temperature may affect the testing or data collected regarding the test specimens 46 during testing in the test chamber 30.

Therefore, the black panel 48 provides the highest temperature that any test specimen 46 may be experiencing during weathering testing in the test chamber 30. The temperature of the black panel 48 is conveyed to the device 20 through the wires 68 so that an operator can monitor the temperature of the black panel 48 with the control panel 28 and adjust the radiance of the lamps 30 accordingly. The adjustment of the radiance may also be accomplished automatically based on the temperature signal from the black panel 48.

Referring to FIG. 5, a black panel assembly 70 constructed in accordance with the teachings of the present disclosure is shown. The black panel assembly 70 includes similar components as the black panel 48. Accordingly, like components are referred to herein with like reference numbers. The black panel assembly 70 includes the black panel 48 which may be similar to or different than the black panel 48 of FIG. 4. In the disclosed examples, the black panel 48 is similar to the black panel 48 of FIG. 4, hence referred to herein with the same reference number. The black panel assembly 70 also includes a platform 72, on which the black panel 48 is mounted with black panel fasteners 74. The platform 72 includes a plurality of standoffs 76 that elevate the black panel 48 relative to a surface on which the standoffs 76 are mounted or placed.

Referring to FIG. 6, in an exploded view of the black panel assembly 70 is shown. Similar to the black panel 48 of FIG. 4, the black panel 48 of the black panel assembly 70 includes an exposure side 60 and a mounting side 61. The temperature sensor housing 62 is mounted on the exposure side 60 with a pair of brackets 64. The temperature sensor housing 62 and the brackets 64 can also be coated with the same black layer as the black panel 48. The temperature sensor housing 62 houses a temperature sensor that detects the temperature of the black panel 48 and conveys that temperature with a signal to the device 20 through the wires 68.

The black panel 48 is mounted on the platform 72 with black panel fasteners 74. The brackets 64 are secured to the exposure side 60 of the black panel 48 with fasteners 66. As shown in FIG. 6, the platform 72 includes an opening 80 which exposes the mounting side 61 of the black panel 48 to a gap 82 when the black panel 48 is mounted on the platform 72. The opening 80 may be any size desired to expose most or portions of the mounting side 61 of the black panel 48 to the gap 82. Because the standoffs 76 elevate the black panel 48 above a surface on which the standoffs 76 are placed or mounted, air can flow through the gap 82. Accordingly, the mounting side 61 of the black panel 48 will also be exposed to the air flow in the gap 82.

Figure 7:
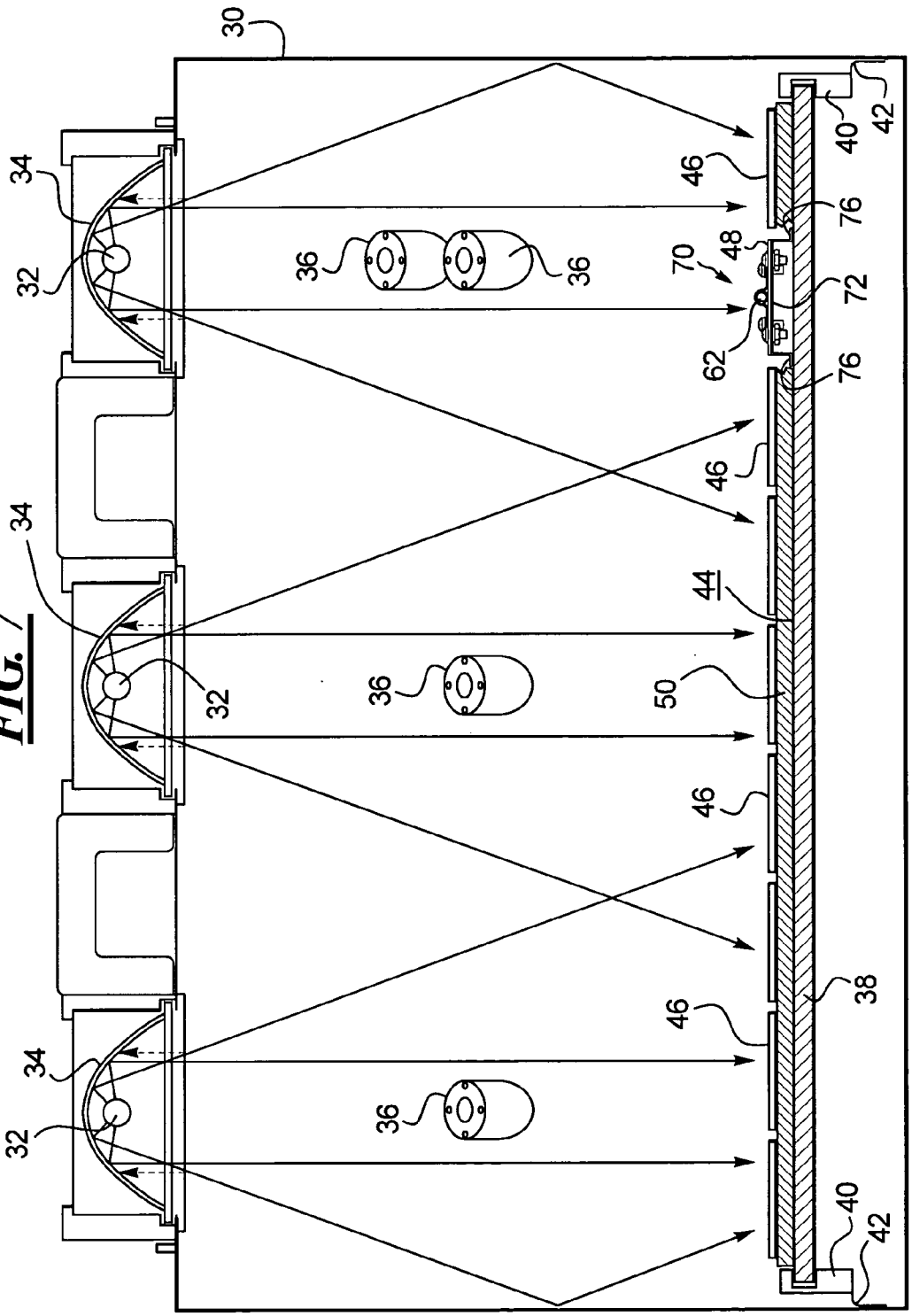
FIG. 7 illustrates a schematic view of the test chamber of FIG. 2 having therein a black panel assembly constructed in accordance with the teachings of the present disclosure.

Referring to FIG. 7, the black panel assembly 70 is shown as installed on the specimen table 38 in the test chamber 30. The standoffs 68 elevate the black panel 48 above the mounting surface 44 of the specimen table 38. Accordingly air can flow in the gap 82, which can allow heat transfer to the mounting side 61 of the black panel 48 primarily by convection rather than conduction. By elevating the black panel 48 with the platform 72, the back side of the black panel 48 of the present disclosure is exposed to the atmosphere of the test chamber 30, which complies with the ASTM 6151 (American Society for Testing and Materials, designation 6151) standard.

Additionally, because the black panel 48 of FIG. 7 is elevated with respect to the mounting surface 44 of the specimen table 38, heat cannot be conducted between the black panel 48 and the specimen table 38. Accordingly, the static and dynamic response of the temperature of the black panel 48 cannot be affected because of heat conduction from the specimen table 38.

Furthermore, while the particular preferred embodiments have been shown and described, it will be obvious to those skilled in the art that changes and modifications may be made without departing from the teaching of the disclosure. The matter set forth in the foregoing description and accompanying drawings is offered by way of illustration only and not as limitation. The actual scope of the disclosure is intended to be defined in the following claims when viewed in their proper perspective based on the related art.

What is claimed is:

1. A black panel assembly for use in an accelerated weathering test device having a specimen table, the black panel assembly comprising:
    a platform disposed on the specimen table, the platform including a plurality of standoffs and a mounting surface, wherein the plurality of standoffs elevate the mounting surface relative to the specimen table;
    a black panel having an exposure side and a mounting side, wherein the black panel is mounted on the platform from the mounting side; and
    a temperature sensor connected to the exposure side of the black panel.

2. The black panel assembly of claim 1, wherein the mounting surface of the platform includes at least one opening to expose a portion of the mounting side of the black panel to a gap between the mounting surface and the specimen table.

3. The black panel assembly of claim 1, wherein the temperature sensor is embedded on the exposure surface of the black panel.

4. The black panel assembly of claim 1, wherein the temperature sensor includes a housing removably connected to the exposure surface of the black panel.

5. An accelerated weathering test device comprising:
    a test chamber having a specimen table;
    at least one lamp assembly disposed in the test chamber and configured to direct irradiance toward the specimen table;
    a platform disposed on the specimen table, the platform including a plurality of standoffs and a mounting surface, wherein the plurality of standoffs elevate the mounting surface relative to the specimen table;
    a black panel having an exposure side and a mounting side, wherein the black panel is mounted on the platform from the mounting side; and
    a temperature sensor connected to the exposure side of the black panel.

6. The device of claim 5, wherein the specimen table is planar and disposed in a substantially horizontal orientation in the test chamber.

7. The device of claim 5, further comprising an array of specimen trays disposed on the specimen table, each of the specimen trays configured to hold a test specimen, wherein the platform is configured to occupy one of the specimen trays.

8. The device of claim 5, wherein the mounting surface of the platform includes at least one opening to expose a portion of the mounting side of the black panel to a gap between the mounting surface and the specimen table.

9. The device of claim 5, wherein the temperature sensor is embedded on the exposure surface of the black panel.

10. The device of claim 5, wherein the temperature sensor includes a housing removably connected to the exposure surface of the black panel.

11. A black panel assembly for use in a test chamber of an accelerated weathering test device having at least one lamp directing irradiance toward a specimen table, the black panel assembly comprising:
    a platform disposed on the specimen table, the platform including a plurality of standoffs and a flat mounting surface, wherein the plurality of standoffs elevate the mounting surface relative to the specimen table to provide a gap between a bottom of the mounting surface and the specimen table, and wherein the standoffs are configured to allow air to flow through the gap;
    a black panel having an exposure side and a mounting side, the black panel configured to be mounted on the platform from the mounting side, the exposure side of the black panel oriented to receive irradiance from the at least one lamp; and
    a temperature sensor connected to the exposure side of the black panel.

12. The black panel assembly of claim 11, wherein the mounting surface of the platform includes at least one opening to expose a portion of the mounting side of the black panel to the gap.

13. The black panel assembly of claim 11, wherein the temperature sensor is embedded on the exposure surface of the black panel.

14. The black panel assembly of claim 11, wherein the temperature sensor includes a housing removably connected to the exposure surface of the black panel.

* * * * *

UNITED STATES PATENT AND TRADEMARK OFFICE
CERTIFICATE OF CORRECTION

PATENT NO.       : 7,222,548 B2
APPLICATION NO.  : 11/082594
DATED            : May 29, 2007
INVENTOR(S)      : Waas et al.

It is certified that error appears in the above-identified patent and that said Letters Patent is hereby corrected as shown below:

On the Title Page, Item (75)
Correct Name of First Named Inventor: Chris Waas

Signed and Sealed this

Eleventh Day of December, 2007

JON W. DUDAS
*Director of the United States Patent and Trademark Office*